United States Patent [19]

Nickerson et al.

[11] Patent Number: 5,151,178
[45] Date of Patent: * Sep. 29, 1992

[54] AXIALLY-DRIVEN VALVE CONTROLLED TRAPPING ASSEMBLY

[75] Inventors: Mark A. Nickerson; John S. Poole; Lenore G. R. Frank, all of Landenberg, Pa.

[73] Assignee: Hewlett-Packard Company, Palo Alto, Calif.

[*] Notice: The portion of the term of this patent subsequent to Apr. 23, 2008 has been disclaimed.

[21] Appl. No.: 659,244

[22] Filed: Feb. 22, 1991

Related U.S. Application Data

[60] Division of Ser. No. 403,024, Aug. 31, 1989, Pat. No. 5,009,778, which is a continuation-in-part of Ser. No. 316,383, Feb. 27, 1989, abandoned.

[51] Int. Cl.$^5$ .............................................. B01D 15/08
[52] U.S. Cl. ............................. 210/198.2; 210/659; 210/137; 55/386; 251/129.25; 251/331; 251/335.2
[58] Field of Search ............... 210/635, 656, 659, 137, 210/198.2; 55/67, 386; 251/129.15, 331, 335.2

[56] References Cited

U.S. PATENT DOCUMENTS

| | | |
|---|---|---|
| 2,294,487 | 9/1942 | Stettner .......................... 251/335.2 |
| 2,415,660 | 2/1947 | Stettner .......................... 251/335.2 |
| 3,429,552 | 2/1969 | Huley ............................... 251/331 |
| 3,459,215 | 8/1969 | Dunn ............................ 137/505.25 |
| 3,510,271 | 5/1970 | Emneus et al. ..................... 23/312 |
| 3,700,005 | 10/1972 | Fletcher ........................... 251/122 |
| 3,740,019 | 6/1973 | Kessell ............................. 251/331 |
| 3,812,398 | 5/1974 | Kozel ............................... 251/331 |
| 4,010,769 | 3/1977 | DeLorenzo ..................... 251/335.2 |
| 4,070,004 | 1/1978 | Friswell .......................... 251/331 |
| 4,168,235 | 9/1979 | Guillemin ....................... 210/198.2 |
| 4,232,696 | 11/1980 | Burris ............................ 251/335.2 |
| 4,286,626 | 9/1981 | Leiber ........................... 251/335.2 |
| 4,288,322 | 9/1981 | Guillemin ....................... 210/198.2 |
| 4,500,432 | 2/1985 | Poole et al. ..................... 210/659 |
| 4,594,159 | 6/1986 | Stalberg ......................... 210/198.2 |
| 4,597,866 | 7/1986 | Couillard ....................... 210/198.2 |
| 4,629,561 | 12/1986 | Shirato ........................... 210/198.2 |
| 4,636,315 | 1/1987 | Allen, Jr. .......................... 210/656 |
| 4,681,142 | 7/1987 | Woeller ........................ 251/129.15 |
| 4,714,234 | 12/1987 | Falk ............................... 251/335.2 |
| 4,806,250 | 2/1989 | Takata et al. ..................... 210/659 |
| 4,828,219 | 5/1989 | Ohmi ............................... 251/331 |
| 4,871,453 | 10/1989 | Kumar ........................... 210/198.2 |
| 4,892,654 | 1/1990 | Nickerson ...................... 210/198.2 |

FOREIGN PATENT DOCUMENTS

| | | |
|---|---|---|
| 2008145 | 9/1971 | Fed. Rep. of Germany ... 210/198.2 |
| 3420815A1 | 5/1986 | Fed. Rep. of Germany ... 210/198.2 |
| 432963 | 10/1967 | Switzerland ..................... 210/198.2 |

OTHER PUBLICATIONS

Saito, "New Pressure Regulating System for Constant Mass Supercritical Flow Chromatography", Chromatographia, vol. 25 No. 9. Sep. 1988 pp. 801–805.
Jahn, "Controlled Back Pressure Valve for Constant Flow and Pressure Programming in Packed Column Supercritical Flow Chromatography", Anal. Chem., 1987, 59, pp. 382–384.
Saito, "Directly Coupled Laboratory Scale Supercritical Fluid Extraction–Supercritical Fluid Chromatography", Journal of Chromatography 332 (1985) pp. 107–116.

(List continued on next page.)

Primary Examiner—Ernest G. Therkorn

[57] ABSTRACT

A solenoid driven valve is disclosed which is adaptable for controlling the introduction of a high pressure fluid into a fluid trapping assembly having an absorption column topped with an annular orifice expansion nozzle. The valve has an inlet port to introduce high pressure fluid, an axially moving solenoid driven pin which engages means to restrict fluid flow into said column. A diaphragm is located within the valve to direct fluid into the column and which separates the fluid in a region of high pressure from ambient pressures.

4 Claims, 3 Drawing Sheets

OTHER PUBLICATIONS

"Direct Coupling of a Dense (Supercritical) Gas Chromatograph to Mass Spectrometer Using a Supersonic Molecular Beam Interface", Rev. Sci. Instrum. 52(9) Sep. 1981 pp. 1283-1295.

Giddings, "High Pressure Gas Chromatography of Nonvolatile Species", Science, vol. 162, pp. 67-73 Oct. 4, 1968.

Tescom Corporation Sales Brochure 26-1600, (publication date is not known) single page reference.

Tescom Corporation Sales Brochure 26-1700, (publication date is not known) single page reference.

Union Molycorp "Lathology" Advertisement (publication date is not known) single page reference.

Van Es et al., *Sample Introduction in High Speed Capillary Gas Chromatography; Input Band Width and Detection Limits*, J. High Resol. Chrom. 10 (1987), No. 5.

Young et al., U.S. PTO Publication *High Temperature Gas Chromatograph Valve*, B528,756 (1976).

AXIALLY-DRIVEN VALVE CONTROLLED TRAPPING ASSEMBLY

This is a division of application Ser. No. 403,024, filed Aug. 31, 1989, now U.S. Pat. No. 5,009,778 issued Apr. 23, 1991 which is a continuation-in-part of Ser. No. 316,383, filed Feb. 27, 1989, now abandoned.

BACKGROUND OF THE INVENTION

This invention relates to trapping assemblies for use with fluid systems and to valve means suitable for use with such assemblies as part of the process for introducing trapped solutes into instruments such as gas, liquid or supercritical fluid chromatographs that are used to measure amounts of such solutes.

The use of gas, liquid and supercritical fluid chromatographs (hereinafter collectively referred to as "chromatographs") have long been used to measure amounts of solutes in fluids. In a gas chromatograph the carrier fluid is gas, e.g., nitrogen, and in a liquid chromatograph it is a liquid, e.g., methyl alcohol. In supercritical fluid chromatographs the carrier fluid is ordinarily a gas, e.g., $CO_2$, which is densified with increased pressure above its critical point. The density and thus the effective solvent power of an supercritical fluid can be controlled by pressure.

It has become increasingly important to be able to measure very small, even trace, amounts of solutes in a carrier fluid. This is particularly desirable in measuring very small amounts of contaminants, such as organic chemicals, pesticides, etc., in drinking water or foods in amounts of the order of 1 ppb. In such circumstances, the amount of solute may be below the minimum detectable quantity (MDQ) for most chromatographs.

In the method and apparatus of Poole et al., U.S. Pat. No. 4,500,432, granted Feb. 19, 1985 there is provided a way to concentrate solutes contained in fluids before they are applied to chromatographs for analysis. In general, the technique of Poole et al. involves concentrating a solute by passing a solvent containing it through a first trapping means (e.g., a packed column) that adsorbs the solute and passes the solvent to waste, passing a fluid (e.g., a supercritical fluid) through the first trapping means to dissolve or solubilize the solute therefrom and carry it into a second trapping means, and reducing the solubility parameter of the fluid in the second trapping means. Where a supercritical fluid carries the solute, the last step can involve passing the fluid from a high pressure to a much lower pressure. This permits the fluid to escape from the second trapping means leaving the solute concentrated therein. The second trapping means can be used by itself when a vessel containing a range of materials (solids, semi-solids, liquids dispersed as a stationary phase) replaces the first trapping means.

Currently known approaches to achieve pressure drops from high pressure systems to lower pressures include: (a) static orifices which are typically holes of about 3 to 20 microns in diameter in thin metal foil or at the end of converging ducts, or (b) lengths of capillary tubing (e.g., 20 to 50 microns ID). Neither of the foregoing decouple control of pressure (and therefore density) from linear flow rate.

Often in larger systems (e.g., small pilot plant scale), conventional needle valves are used for pressure drop. These tend to suffer from large inaccessible volumes (dead volume) and inappropriately placed boundaries to the expanding stream so that sampling of high pressure fluid is not representative. Large valves also tend to suffer from poor design in getting sufficient heat into the device to balance heat lost during expansion and, thus, tend to "ice up" causing erratic flow or stoppages. Available back pressure regulators, using manually set, spring-driven control pistons, do not contain nozzle geometry for sampling with the capability of electronic control of the pressure.

SUMMARY OF THE INVENTION

This invention provides axially-driven valve means which permits back pressure regulation and fast response time and which acts as a variable orifice for transmitting fluids from a high pressure region to a much lower pressure region. This invention further provides an assembly especially useful in the apparatus and method of the type described in Poole et al. since it largely overcomes the disadvantages or shortcomings of known fluid trapping assemblies suitable for use with supercritical fluids. This is accomplished by means suitable for electronic control through axially driven valve means of the expansion of pressurized fluid through an orifice expansion nozzle into a fluid trapping assembly with low dead volume having a column for trapping or accumulating a solute component of said fluid. This invention is more particularly pointed out in the appended claims and is described in its preferred embodiments in the accompanying drawings and the detailed description thereof.

DETAILED DESCRIPTION OF THE INVENTION

Figure 1:
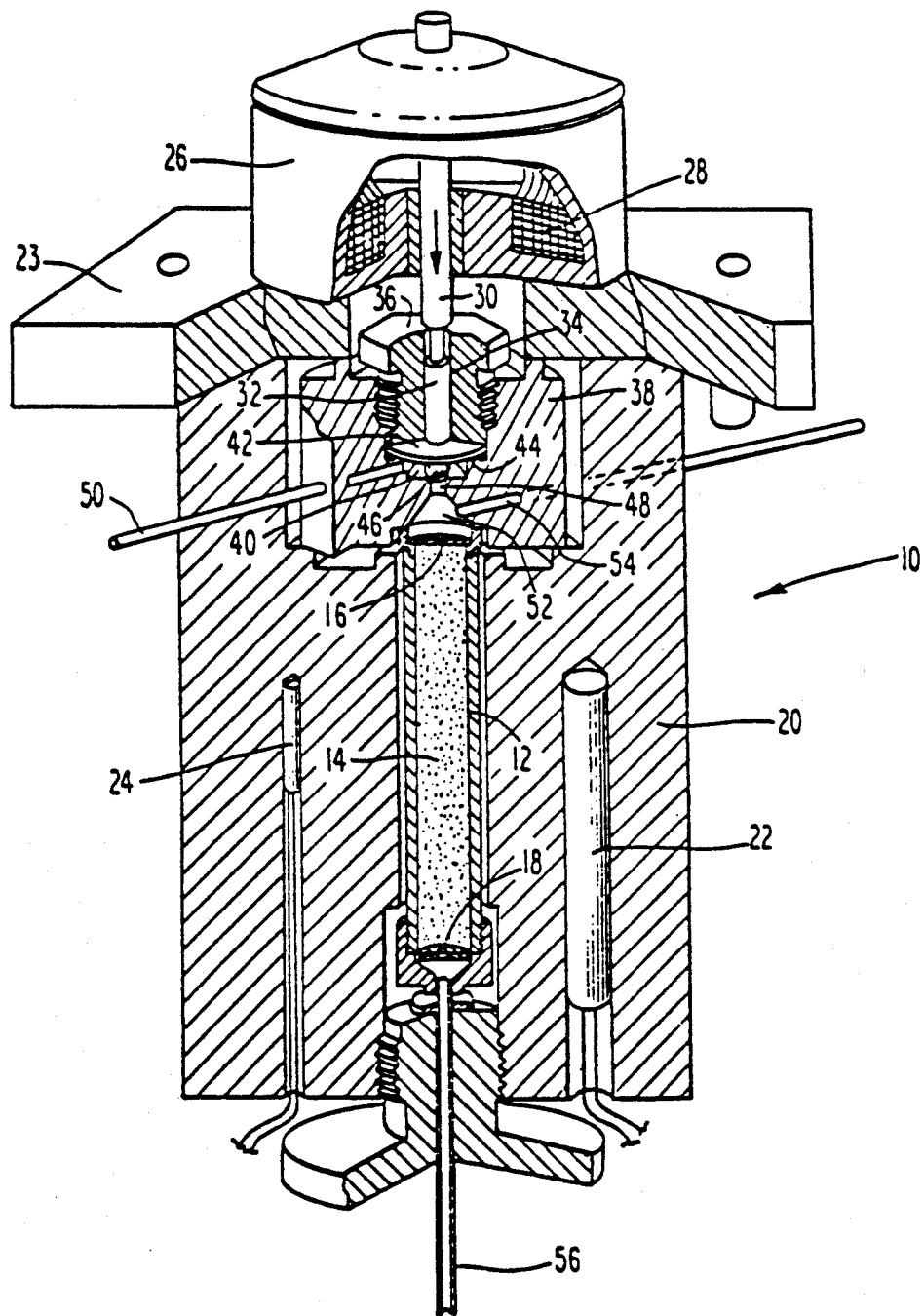
FIG. 1 is a partial cross-section of a fluid trapping assembly and valve in accordance with this invention.

Referring now to the drawings, trapping assembly 10 contains a column 12 which is filed with packing material 14. Suitable packing material includes a wide variety of materials, e.g., metal cylinders, beads, spheres or particles which can suitably be made of stainless steel, nickel, nickel-copper, nickel chrome, cobalt chrome, etc. Other packing materials are glass or resin beads, particles, etc., sintered porous metal matrix of irregular or spherical metal, or silica or bonded-phase-silica and polymeric particles, beads, etc. It is also possible that the column can be unpacked and/or have an interior coating of a polymer such as are known in the art of chromatography.

The column 12 is provided at top and bottom with suitable layers of frit 16 and 18 which can be a porous layer of stainless steel particles.

The column 12 is shown encased in housing 20 which is provided with electric heating element 22 and thermocouple 24. At the top of housing 20 is plate 23. Mounted atop plate 23 is solenoid 26 shown partially cut away in FIG. 1 revealing windings 28 and axially moving shaft 30 reactive to the electric current flowing in the solenoid 26.

Axially extending from shaft 30 is a pin 32 which extends through an axially located opening 34 in threaded bushing 36. The bushing 36 is threadably engaged in a central opening located in valve block 38 located within housing 20 atop column 12. Located within valve block 38 below the bushing 36 is valve chamber 40. At the top of valve chamber 40 is diaphragm 42 which is held in sealed engagement between the end of bushing 36 and annular shoulder 44 of the valve block 38 surrounding valve chamber 40.

The diaphragm 42 is ordinarily formed from a hard metal material. The annular edges of the pin 32 and opening 34 are rounded at the diaphragm end thereof.

Located within the valve chamber 40 in FIG. 1 is a spherical metal ball 46, e.g., a ball bearing, the apex of which is welded to the center of the bottom side of diaphragm 42. The ball 46 is adapted to engage and seal fluid exit orifice 48 located centrally at the base of valve chamber 40. The metal of the valve block at the top of orifice 48 should be softer than that of the ball 46 to permit the latter to form a seat.

Extending through the housing 20 and valve block 38 into said valve chamber 40 is inlet 50 which permits introduction of fluid at high pressure into the valve chamber 40.

At the bottom of orifice 48 is a conical diverging section 52 of the nozzle formed therefrom. It is preferred that the angle of the cone be between about 50 to 70 degrees. A design of 65 degrees has been found to be satisfactory. At one side of conical diverging section 52 a flushing port 54 is provided. At the base of column 12 is column outlet 56. Normally, flushing port 54 is closed.

Electrical actuation of solenoid 26 provides axial movement to pin 32 against diaphragm 42. When pin 32 moves downward, ball 46 seals orifice 48. When fluid under pressure flows into inlet 50, pressure is exerted on the bottom of diaphragm 42. Fluid pressures between 1000 and 6000 psi are typical. If the pressure on the diaphragm is sufficient, it and the ball 46 are lifted from orifice 48 and a gap between the ball and the orifice is formed. The diaphragm directs the flow of fluid through the valve chamber 40 and the gap and out through orifice 48. The diaphragm seals off the high pressure fluid from ambient pressure regions within the apparatus. The active diameter of the diaphragm may be about 5 mm and the thickness may be approximately 0.14 mm and made of HAVAR cobalt-nickel-chrome alloy (although other metals such as 440 C and 17-7 Ph stainless steel can be used). The 440 C stainless steel ball may be 2.5 mm in diameter and affixed to the diaphragm by means of brazing (although spot welding or laser welding might be employed). Orifice 48 may be about 1 mm in diameter. The fluid passing through orifice 48 continues to expand in conical diverging section 52 to a region of lower pressure. If the fluid is a gas, e.g., carbon dioxide, held at temperatures and pressures above its critical point, the high density thereof increases its solubility parameter for the dissolved solute therein. When the fluid passes into the column 12 at a much lower pressure, the solute comes out of solution and is removed and collected (which includes being absorbed, or otherwise retained on the packing within the column). The fluid, e.g., carbon dioxide at lower pressure can be removed from the column through outlet 56.

Thereafter, the column can be flushed by introducing fluid through flushing port 54 and removing it through outlet 56 or the direction of flow can be reversed if desired.

Figure 2:
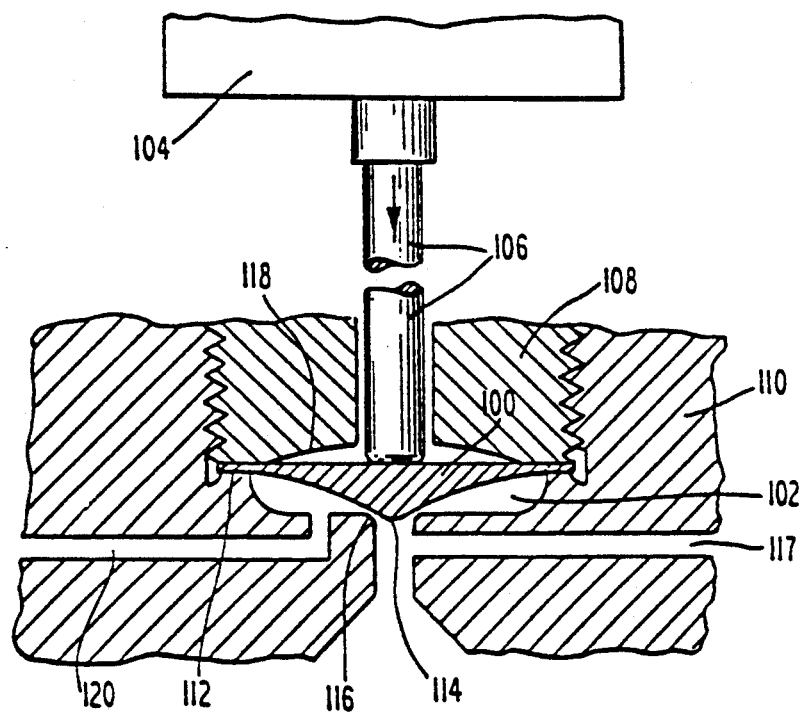
FIG. 2 is a partial cross-section of a valve in accordance with this invention having a flattened conical diaphragm.

Referring now to FIG. 2, a semi-schematic arrangement of a preferred valve means of this invention is shown. The main feature of this embodiment is the use of an inverted, flattened conical diaphragm 100 within valve chamber 102. The solenoid 104, pin 106, bushing 108, valve block 110, inlet 120 and flushing port 117 are similar to those described in connection with FIG. 1.

In the valve means shown in FIG. 2, the flattened conical diaphragm 100 is held in sealing engagement between bushing 108 and valve block shoulder 112 in a similar fashion to diaphragm of FIG. 1. The diaphragm 100 is mounted so that the apex 114 of the conical portion is pointed downward within valve chamber 102. The active diameter of diaphragm 100 may be about 8 mm with a thickness at the outer edge similar to diaphragm 42 of FIG. 1. At the center the thickness may be about 0.9 mm with an included angle of about 120° where it contacts orifice 116. The material is typically 17-7 Ph stainless steel but could also be HAVAR or 440 C stainless steel. Apex 114 is adapted to engage the seat formed in the upper end of orifice 116. Again, the metal of diaphragm 100 is harder than that of the seat to provide for sealed engagement when closed.

The bottom surface 118 of bushing 108 is formed hemispherically. In case of power failure in the solenoid, the force of the fluid in inlet 120 will force diaphragm 100 upward to be held securely against surface 118 without significant deformation. Optionally, pin 106 may be secured to diaphragm 100.

Figure 3:
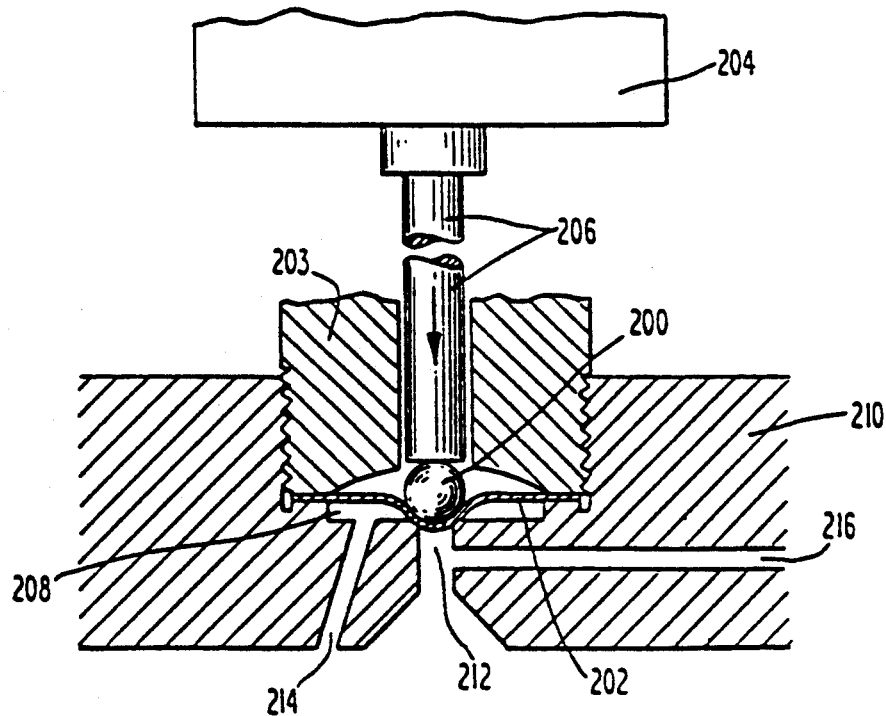
FIG. 3 is a partial cross-section of a valve in accordance with this invention having a metal ball located above the diaphragm.

Referring to FIG. 3 a valve means is shown wherein a metal ball 200 is shown located above diaphragm 202. The bushing 203, solenoid 204, pin 206, valve chamber 208, and valve bock 210 are similar to those described in connection with FIG. 1. In this embodiment the pin 206 acting on and through ball 200, forces the depressed center of diaphragm 202 against the orifice 212 in sealing engagement. Diaphragm 202 is of similar geometry and material to diaphragm 42 of FIG. 1. The design may be an inversion of that in FIG. 1 so as to eliminate the need for attaching the ball to the diaphragm. The bottom surface of bushing 203 is formed hemispherically in the same manner as shown by 118 for FIG. 2 for the same purpose. Fluid inlet 214 and a flushing port 216 are also provided.

Figure 4:
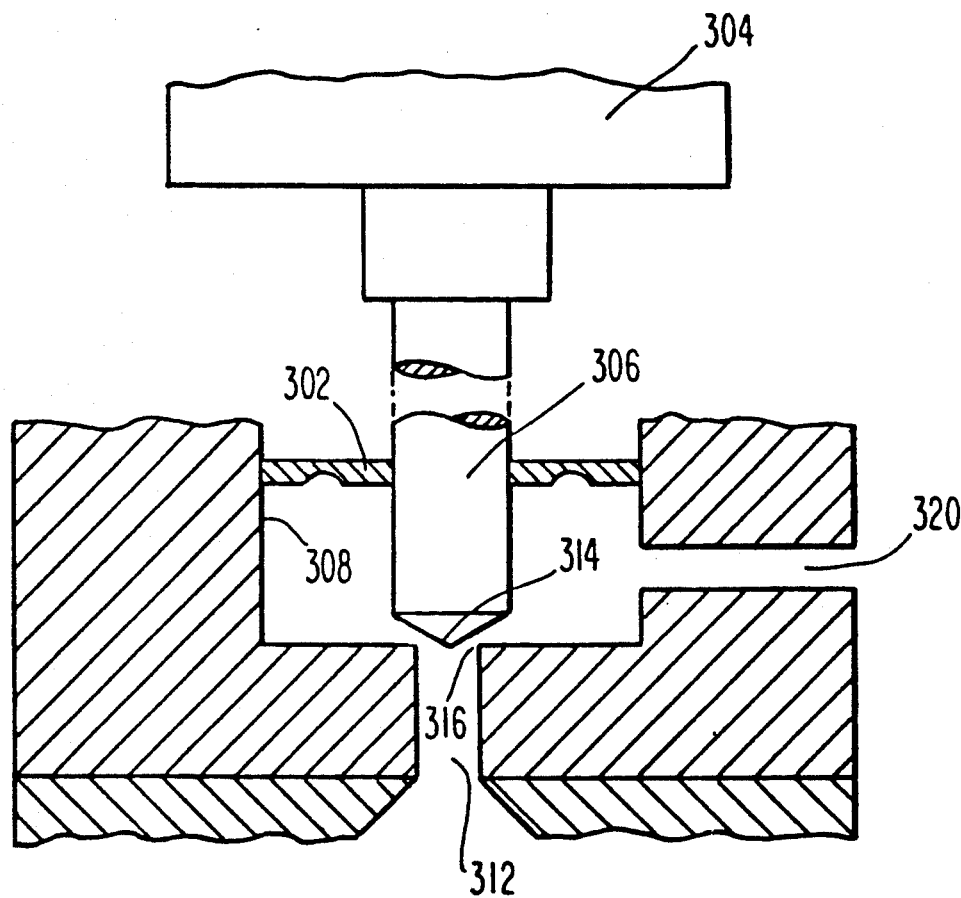
FIG. 4 is a partial cross-section of a valve in accordance with this invention having a pin with a point.

Referring to FIG. 4, a valve means is shown wherein the pin 306 is shown to be actuated by solenoid 304. The pin 306 has a conical point or apex 314 adapted to engage the seat formed in the upper end 316 of orifice 312 in sealed engagement when closed. Fluid at high pressure may be introduced through inlet 320 and exit through orifice 312 and its conical expansion nozzle. A diaphragm 302 in the form of an O-ring seal or washer is shown to be attached to the interior chamber surface 308. The diaphragm 302 has a central aperture through which the pin 306 is located. The diaphragm 302 surrounds the pin 306 in sealing engagement which permits the pin 306 to slide axially in its movement to open and close orifice end 316. Suitable materials for the diaphragm 302 include fluorocarbon polymers and elastomers such as those sold under the trademarks TEFLON, KEL-F, or PEEK.

In each embodiment of valve means of this invention, the diaphragm separates high pressure fluids from ambient pressure regions, locates the means that blocks the orifice, and lifts the means that blocks the orifice in response to force from the high pressure fluid acting against the diaphragm. The valve means of this invention are especially useful in supercritical fluid trapping means described herein and especially for use in the invention of Poole et al. U.S. Pat. No. 4,500,432. Such valves are, however, useful in any device where high pressure fluids are to be directed through a variable orifice to a region of lower pressure, and which are to be operated by electronic control (e.g., the connection between the outlet of a supercritical fluid chromatograph column and a detection means).

The valves illustrated herein are actuated by solenoid means; however, such valves can be also be axially driven by linear motors, piezo electric or magneto-strictive linear movement devices, and electrically actuated, thermally expanded linear movement devices. A function which can be achieved in accordance with this invention is the expansion of fluids and fluid mixtures from high pressures to low pressures where the range of said fluids and mixtures includes supercritical fluids, nearly critical fluids, subcritical fluids, gases and liquids. Devices of this invention may be used to maintain or control pressure and/or to sample fluid from extraction devices, chromatographs, or fluid reservoirs. One feature of the design is to allow minimal distances from the annular throat of the nozzle to possible downstream devices, e.g., detectors (like mass spectrometer inlet systems, flame ionization detectors), supersonic molecular beam formation systems, and/or effluent collection devices. Nozzle designs may also include annular-orifice, variable annular orifice, open orifice, compliant open orifices, or slit aperatures.

We claim:
1. In a trapping assembly for use with fluid systems having a vessel at least partially packed with a material for removing a solute component of said fluid, the combination comprising:
   an inlet for introducing the fluid under pressure into the trapping assembly;
   an axially driven valve for controlling the mass flow of the fluid through the inlet, and
   an annular orifice expansion nozzle leading from the valve to the vessel, wherein the valve is actuated and comprises an axially moving pin adapted to restrict the mass flow of the fluid through the valve by varying the size of the annular orifice in the expansion nozzle.

2. The trapping assembly of claim 1 wherein the vessel is a column and the material packed in the column comprises a solid phase packing material.

3. A chromatography column for conducting fluid under high pressure and collecting solute components dissolved from the fluid comprising:
   variable restriction orifice of a preselected size comprising an expansion nozzle disposed atop the column sized and dimensioned to allow the fluid to expand into the column under reduced pressure and the solute components to precipitate and be collected.

4. The column of claim 3 wherein the variable restriction orifice comprises an axially driven valve wherein the mass flow of the fluid into the column is restricted by the action of the axially driven valve.

* * * * *